US00PP20142P2

(12) United States Plant Patent
Klemm

(10) Patent No.: US PP20,142 P2
(45) Date of Patent: Jun. 30, 2009

(54) ***PETUNIA* PLANT NAMED 'KLEPH07134'**

(50) Latin Name: *Petunia hybrida*
Varietal Denomination: KLEPH07134

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/082,135

(22) Filed: Apr. 9, 2008

(51) Int. Cl.
*A01H 5/00* (2006.01)

(52) U.S. Cl. ..... Plt./356

(58) Field of Classification Search ..... Plt./356
See application file for complete search history.

*Primary Examiner*—Susan B McCormick Ewoldt
(74) *Attorney, Agent, or Firm*—Jondle & Associates, P.C.

(57) ABSTRACT

A new cultivar of *Petunia* particularly characterized by a compact, semi-upright and mounding growth habit and bright pink, large flowers, is disclosed.

1 Drawing Sheet

Genus and species: *Petunia* hybrid.
Variety denomination: 'KLEPH07134'.

BACKGROUND OF THE NEW PLANT

The present invention comprises a new and distinct cultivar of *Petunia*, botanically known as *Petunia* hybrid, and hereinafter referred to by the cultivar name 'KLEPH07134'. 'KLEPH07134' was discovered as a seedling resulting from a cross conducted in summer 2004 in Stuttgart, Germany between the proprietary female *Petunia* parent, 'W 077' (unpatented) and the proprietary male *Petunia* parent, 'W 054' (unpatented). A single plant selection was subsequently chosen for further evaluation and for asexual propagation.

The new cultivar was created in 2004 in Stuttgart, Germany and has been asexually reproduced repeatedly by vegetative cuttings and in-vitro propagation in Stuttgart, Germany over a two and one-half-year period (more than 30 generations). 'KLEPH07134' has been found to retain its distinctive characteristics through successive asexual propagations.

SUMMARY OF THE INVENTION

The following are the most outstanding and distinguishing characteristics of this new cultivar when grown under commercial practices in a greenhouse in Stuttgart, Germany.

1. A compact, semi-upright and mounding growth habit; and
2. Bright pink, large flowers.

DESCRIPTION OF THE PHOTOGRAPH

This new *Petunia* plant is illustrated by the accompanying photograph which shows a close-up of the mature flower; the colors shown are as true as can be reasonably obtained by conventional photographic procedures. The photograph is of a plant about 5-months old and grown from rooted cuttings in an 11-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPH07134'. The data which define these characteristics were collected from asexual reproductions carried out in Stuttgart, Germany. The plant history was taken on 5-month old plants in 11-cm pots that were pinched once approximately one week after potting and grown in a greenhouse in the spring. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Solanaceae.
- *Genus and species.*—*Petunia* hybrid.
- *Common name.*—*Petunia*.

Parentage:
- *Female parent.*—The proprietary *Petunia* parent, 'W 077' (unpatented).
- *Male parent.*—The proprietary *Petunia* parent, 'W 054' (unpatented).

Plant:
- *Form.*—Compact and mounding.
- *Habit.*—Semi-upright.
- *Height* (*from top of soil*).—18.0 cm.
- *Width* (*horizontal plant diameter*).—22.0 cm.
- *Propagation.*—Vegetative propagation by cuttings or in-vitro propagation.
- *Time to produce a finished flowering plant.*—13 weeks.
- *Time to initiate and develop roots.*—21 days.
- *Root description.*—Moderate density and freely branching, while roots.

Stems:
- *Average number* (*basal*).—6.
- *Length of basal branches* (*from the base of the stem to the tip*).—15 cm.
- *Internode length.*—0.5 cm to 2.0 cm.
- *Diameter of branches* (*from midpoint*).—2.0 cm to 6.0 cm.
- *Stem color.*—RHS 137C.

*Anthocyanin.*—Absent.
*Texture.*—Smooth.

Leaves:
*Arrangement.*—Alternate.
*Size.*—Length: 1.0 cm to 3.0 cm. Width: 0.5 cm to 2.5 cm.
*Shape.*—Broadly elliptic.
*Margin.*—Very weak undulation.
*Apex.*—Acute.
*Base.*—Obtuse.
*Immature leaf.*—Color: Upper surface: RHS 138A. Lower surface: RHS 138C.
*Mature leaf.*—Color: Upper surface: RHS 146A. Lower surface: RHS 146B.
*Texture* (*both surfaces*).—Smooth.
*Venation.*—Pinnate.
*Venation color.*—Upper surface: RHS 145A. Lower surface: RHS 145B.
*Petioles.*—Length: 0.3 cm to 2.0 cm. Diameter: 0.2 cm. Color (both upper and lower parts): RHS 138B. Texture: Smooth.

Flower bud:
*Shape.*—Irregular, oblong.
*Size.*—Length: 4.0 cm. Diameter: 0.8 cm.
*Color at tight bud.*—RHS 154C.
*Immature flower color.*—RHS 67A and RHS 2D.

Inflorescence:
*Blooming habit* (*flowering season*).—Blooms during the summer.
*Inflorescence type.*—Single flower.
*Number of flowers per node.*—1.
*Lastingness of individual blooms on the plant.*—7 days.
*Fragrance.*—Absent.
*Pedicels.*—Color: RHS 137C. Length: 2.0 cm. Diameter: 0.3 cm.
*Texture.*—Smooth.

Flowers:
*Shape.*—Cup-shaped.
*Size.*—Diameter (flower face): 6.5 cm. Depth (total length of flower): 4.5 cm. Funnel: Length: 3.5 cm. Diameter (at opening): 1.0 cm. Outside texture: Moderate.
*Mature flower.*—Face/Margin Color: Upper surface: RHS 67B. Lower surface: RHS 4C. Corolla: Shape of corolla: Cup-shaped. Color inside (throat): RHS 2B. Color outside: RHS 4C. Petals: Apex: Rounded to emarginate. Base; Reniform. Margin: Undulating. Waviness: Weak. Lobation: Moderate. Texture: Strong.
*Calyx arrangement.*—One star-shaped calyx tube with five sepals fused at the base per flower.
*Sepals.*—Number. 5. Color (both surfaces): RHS 138A. Length: 2.0 cm. Width: 0.5 cm. Shape: Lanceolate to elliptic. Apex: Obtuse. Base: Fused. Margin: Entire. Texture (both surfaces): Smooth.

Reproductive organs:
*Stamens.*—Quantity: 5. Shape: Elliptic. Filament color: RHS 150A. Filament length: 0.5 cm. Filament diameter: 0.1 cm. Anther: Shape: Elliptic. Color: RHS 2D. Length: 0.3 cm. Diameter: 0.2 cm. Pollen: Color: RHS 2D. Amount: Abundant.
*Pistils.*—Number: 1. Length: 0.5 cm. Diameter: 0.1 cm. Stigma: Color: RHS 150A. Shape: Oval. Length: 2 cm. Diameter: 0.1 cm. Style: Color: RHS 150C. Length: 2.0 cm. Diameter: 0.1 cm. Shape: Fibrous.

Fruit and seed set: None observed.
Disease and insect resistance: Not observed.

COMPARISON WITH PARENTAL AND COMMERCIAL CULTIVARS

'KLEPH07134' differs from the female parent, the proprietary *Petunia* 'W 077' (unpatented) in that 'KLEPH07134' has a compact and mounding growth habit and large flowers, while 'W 077' has a flat and trailing growth habit and average-sized flowers.

'KLEPH07134' differs from the male parent, the proprietary *Petunia* 'W 054' (unpatented) in that 'KLEPH07134' has a compact and mounding growth habit, while 'W 054' has a semi-trailing growth habit.

'KLEPH07134' differs from the commercial comparison variety 'Famous Cerise Pearl' (unpatented) in that 'KLEPH07134' has a compact and mounding growth habit, while 'Famous Cerise Pearl' has an upright, wild, and very vigorous growth habit.

I claim:

1. A new and distinct cultivar of *Petunia* plant as shown and described herein.

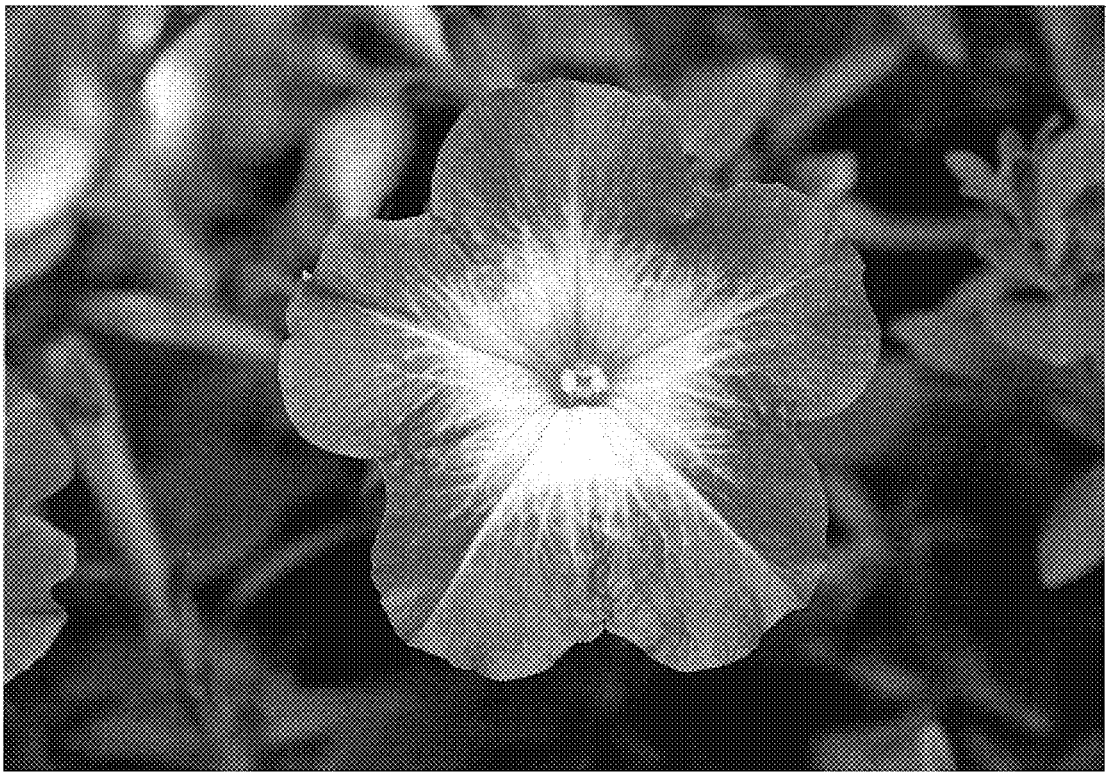

* * * * *